United States Patent [19]

Schwierz et al.

[11] 4,176,279
[45] Nov. 27, 1979

[54] TOMOGRAPH FOR PRODUCING TRANSVERSE LAYER IMAGES

[75] Inventors: Günter Schwierz; Wolfgang Häerer, both of Erlangen, Fed. Rep. of Germany

[73] Assignee: Siemens Aktiengesellschaft, Berlin & Munich, Fed. Rep. of Germany

[21] Appl. No.: 896,396

[22] Filed: Apr. 14, 1978

[30] Foreign Application Priority Data

May 24, 1977 [DE] Fed. Rep. of Germany ....... 2723401

[51] Int. Cl.² ............................................... A61B 6/00
[52] U.S. Cl. .................................................. 250/445 T
[58] Field of Search .................................... 250/445T

[56] References Cited

U.S. PATENT DOCUMENTS

| 3,983,398 | 9/1976 | Boyd | 250/445 T |
| 4,101,768 | 7/1978 | Lill | 250/445 T |
| 4,115,698 | 9/1978 | Hounsfield | 250/445 T |
| 4,149,079 | 4/1979 | Ben-Zeev et al. | 250/445 T |

Primary Examiner—Alfred E. Smith
Assistant Examiner—T. N. Grigsby
Attorney, Agent, or Firm—Hill, Van Santen, Steadman, Chiara & Simpson

[57] ABSTRACT

In an illustrated embodiment, the fan shaped beam of penetrating radiation has a central ray directed offcenter relative to a row of detectors e.g. by a distance corresponding to one-fourth the detector separation. In this way, for each projection with a given central ray angle, further points can be derived by interpolation using the measurements from other projections. With a given number of detector elements, the number of points per projection can be doubled in this way.

4 Claims, 8 Drawing Figures

TOMOGRAPH FOR PRODUCING TRANSVERSE LAYER IMAGES

BACKGROUND OF THE INVENTION

The invention relates to a tomographic apparatus for producing transverse layer images of a radiography subject, with a patient couch, with a radiation measuring arrangement comprising a radiation source producing a fan-shaped beam of rays which penetrates the radiography subject and whose cross sectional extent perpendicular to the layer plane is equal to the layer thickness and the beam transverse extent being of such a magnitude in the layer plane that the whole radiography subject is penetrated, and a radiation receiver consisting of a row of detector elements, which detects the radiation intensity behind the subject, with a rotating device for the measuring arrangement and with a computer for the transformation of the signals supplied by the radiation receiver into a tomographic layer image.

A tomographic apparatus of this kind is described for example in the German Offenlengungsschrift 25 53 187. In this type of tomographic apparatus the scanning of a patient is carried out by rotating the measuring arrangement through an angle of, for example, 360°. During this rotation the radiation receiver can be periodically interrogated at equal intervals of time. The number of measured values per scanning process is therefore given by the number of the interrogation processes of the radiation receiver; i.e., by the number of the projections and the number of detector elements in the radiation receiver.

In order to achieve a good image quality it is necessary, on the one hand, to select a sufficiently high number of projections, but on the other hand also to provide a sufficiently high number of detector elements in the radiation receiver. It is not possible however for the number of detector elements in the radiation receiver to be increased indefinitely.

SUMMARY OF THE INVENTION

The underlying object of the invention is to produce a tomographic apparatus of the initially cited type with which, with a relatively low number of detector elements in the radiation receiver, a relatively large amount of data is available for the image calculation per projection.

This object is achieved according to the invention in that the radiation receiver is arranged so that its axis of symmetry and the axis of symmetry of the x-ray beam are offset at a distance from each other in the layer plane. In the tomographic apparatus according to the invention, it is possible to calculate for a specific projection, by means of interpolation, data for the image calculation which originate from other projections. In this way, without increasing the number of detector elements, a substantial improvement of the image is achieved in comparison to the case where the axis of symmetry of the radiation receiver coincides with the axis of symmetry of the x-ray beam. A particularly advantageous development consists in selecting the distance of offset so that it corresponds to a quarter of the detector element separation.

The invention is hereafter described in more detail with reference to an exemplary embodiment represented in the accompanying sheets of drawings; and other objects, features and advantages will be apparent from this detailed disclosure and from the appended claims.

DETAILED DESCRIPTION

Figure 1B:
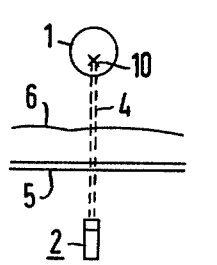
FIG. 1 comprises a diagrammatic cross-sectional view labeled FIG. 1A and a longitudinal partial schematic view labeled FIG. 1B, showing tomographic apparatus for producing transverse layer images.
Figure 1A:
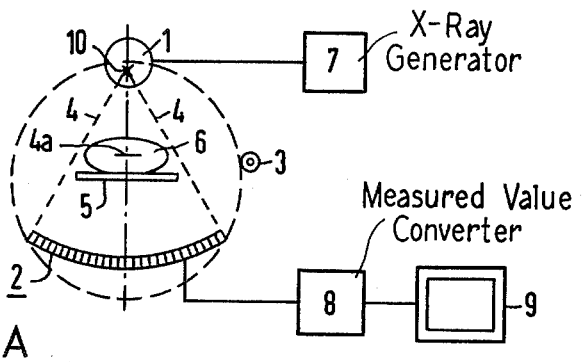

The tomographic apparatus shown in FIG. 1 has a radiation measuring arrangement which consists of an x-ray tube 1 and a radiation receiver 2. By means of a schematically represented rotational drive device 3, the radiation measuring arrangement 1, 2 can be rotated about a longitudinal axis 4a. The x-ray tube 1 emits a fan-shaped x-ray beam 4 which totally penetrates in a transverse layer a patient 6 lying on a couch 5. It can be seen from the side view in FIG. 1B that the cross-section of the x-ray beam 4 perpendicular to the penetrated layer is equal to the layer thickness. The x-ray tube 1 is supplied by an x-ray generator 7 with high voltage. The output signals of the radiation receiver 2 are processed by a measured value converter 8 which calculates therefrom an image in the form of a matrix of image point data. This image is reproduced on a display unit 9. The radiation receiver 2 consists of a row of detector elements. The number of detector elements is selected in accordance with the desired image definition and is over 100 on the order of magnitude.

In order to produce a transverse layer image, the measuring arrangement 1, 2 is rotated by means of the rotary drive device 3 through 360° around the patient 6. At predetermined positions, e.g. at each degree of angle, the output signals of the detector elements of the radiation receiver 2 are thereby transmitted to the computer of measured value converter 8.

Figure 2:
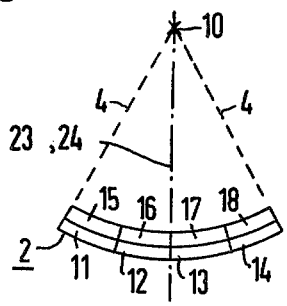
FIG. 2 shows a schematic representation of the radiation measuring arrangement in the case of the tomographic apparatus according to FIG. 1.

In order to illustrate the fundamental mode of operation, FIG. 2 represents the focus 10 of the x-ray tube 1 and the fan-shaped x-ray beam 4. In order to illustrate the principle, it is sufficient if, according to FIG. 2, only four detector elements 11, 12, 13, 14 are shown by way of example in the radiation receiver 2. A collimator element 15 to 18 lies before each detector element 11 to 14.

FIG. 3 again shows the focus 10 of the x-ray tube 1 and the central radiation path or axis 24 associated with four detector elements having a central axis 23. Thus four measured value points 19 to 22 are represented corresponding to the four detector elements taken as a basis. If it is conceived that a perpendicular line is drawn from the coordinate origin Z representing the center of rotation of the central ray of the x-ray beam and that the measured value is plotted at the foot of the perpendicular, then the four measured values lie on a circle T which is drawn through origin Z and the position of the focus 10 which is under consideration.

Figure 3:
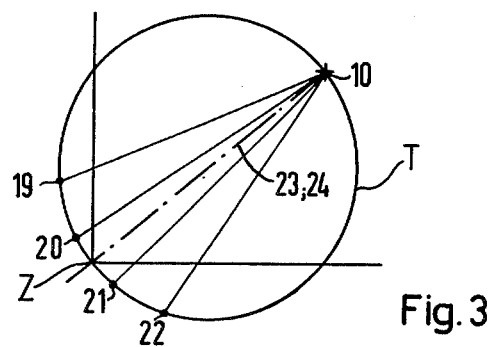
FIGS. 3 and 4 show representations for illustrating how the data is obtained.
Figure 4:
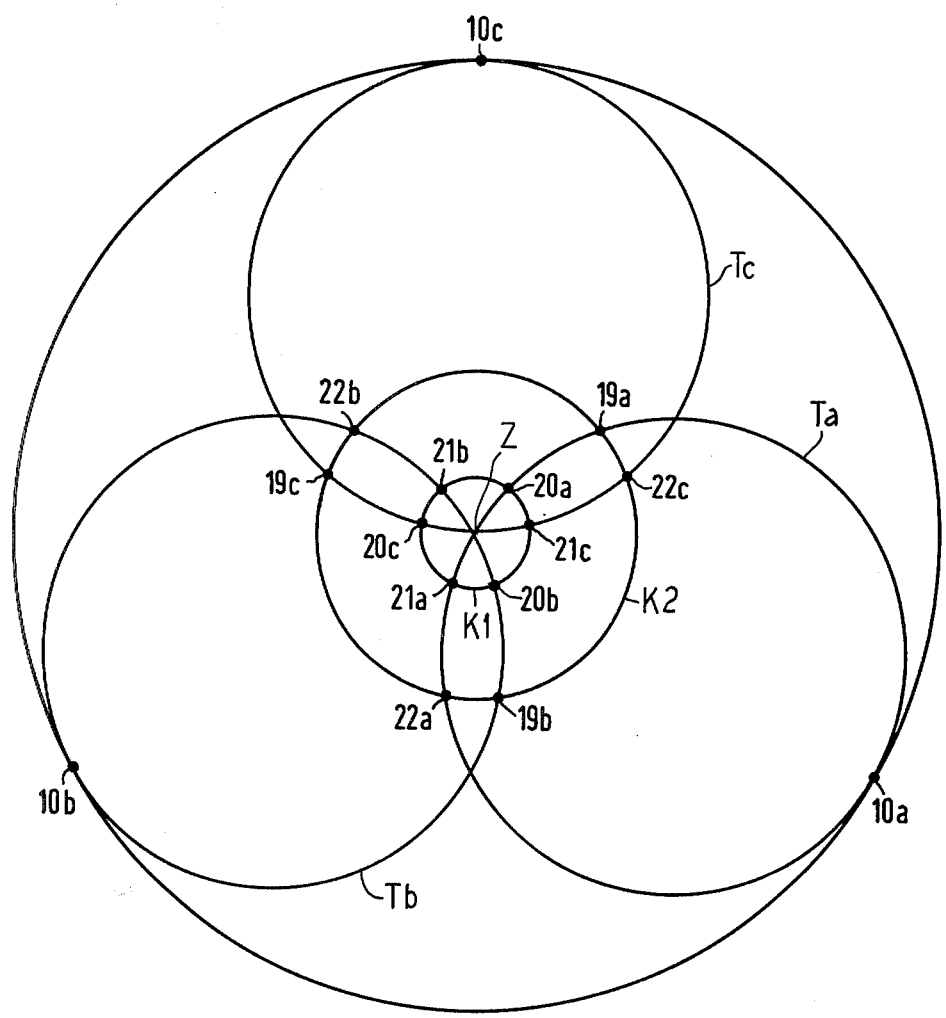

FIG. 4 shows the representation according to FIG. 3 for three different positions of the focus 10; namely, the positions 10a to 10c, thus three different projections. In accordance with this, three different positions are obtained for the measured value points, designated by 19a to 22a, 19b to 22b and 19c to 22c lying on the respective circles Ta, Tb, and Tc. It can be seen from FIG. 4 that all the measured value points lie on two measured value circles K1 and K2 and are distributed unequally over the plane shown (the socalled Radon plane) which corresponds to the layer plane of the irradiated object. This unequal distribution is one of the reasons for artifacts in the image calculated by the computer of converter 8 in the case of the known x-ray tomographic apparatus.

According to FIG. 2 in the known x-ray tomographic apparatus the axis of symmetry (designated 23) of the radiation receiver 2 coincides with the axis of symmetry (designated 24) of the x-ray beam 4. Because of this fact there results the distribution represented in FIG. 4, of the measured value points 19a to 22c on two measured value circles K1 and K2.

Figure 5:
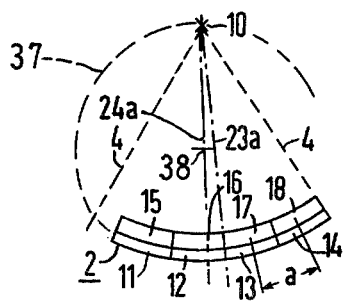
FIG. 5 (on sheet one of the drawings) shows the radiation measuring arragement of a tomographic apparatus according to the invention.
Figure 6:
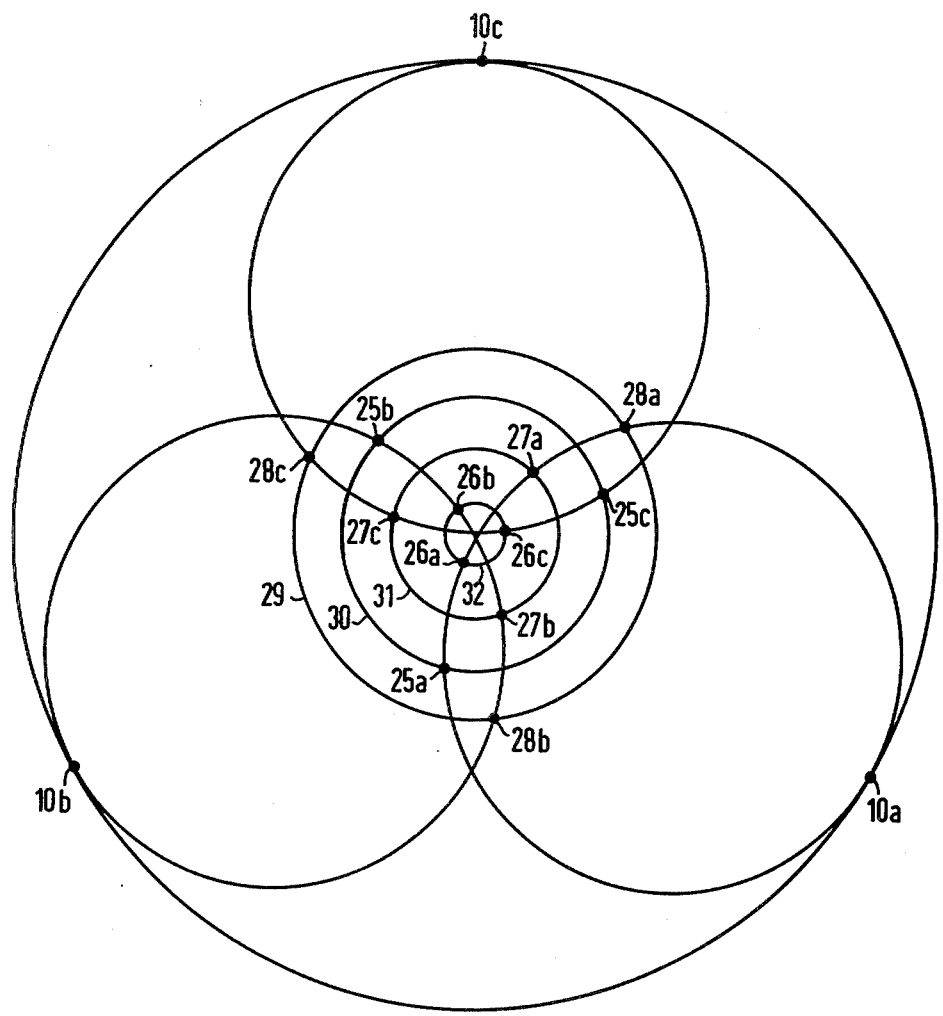
FIGS. 6 and 7 show representations for illustrating data acquisition in the case of a tomographic apparatus according to FIG. 5.

FIG. 5 (on sheet one of the drawings) now shows a measuring arrangement in the case of which the radiation receiver 2 is disposed so that its axis of symmetry 23a and the axis of symmetry 24a of the x-ray beam 4 are offset at a distance from each other in the layer plane (and as measured at the detector) which corresponds to a quarter of the center to center detector element distance a. FIG. 6 again represents the distribution of the measured value points in the Radon plane. The measured value points 25a to 28a are obtained for the focus position 10a, the measured value points 25b to 28b for the focus position 10b and the measured value points 25c to 28c for the focus position 10c. It can be seen from FIG. 6 that in the case of the shown mutual displacement of the two axes of symmetry 23a and 24a, all the measured value points are on four measured value circles 29 to 32.

Figure 7:
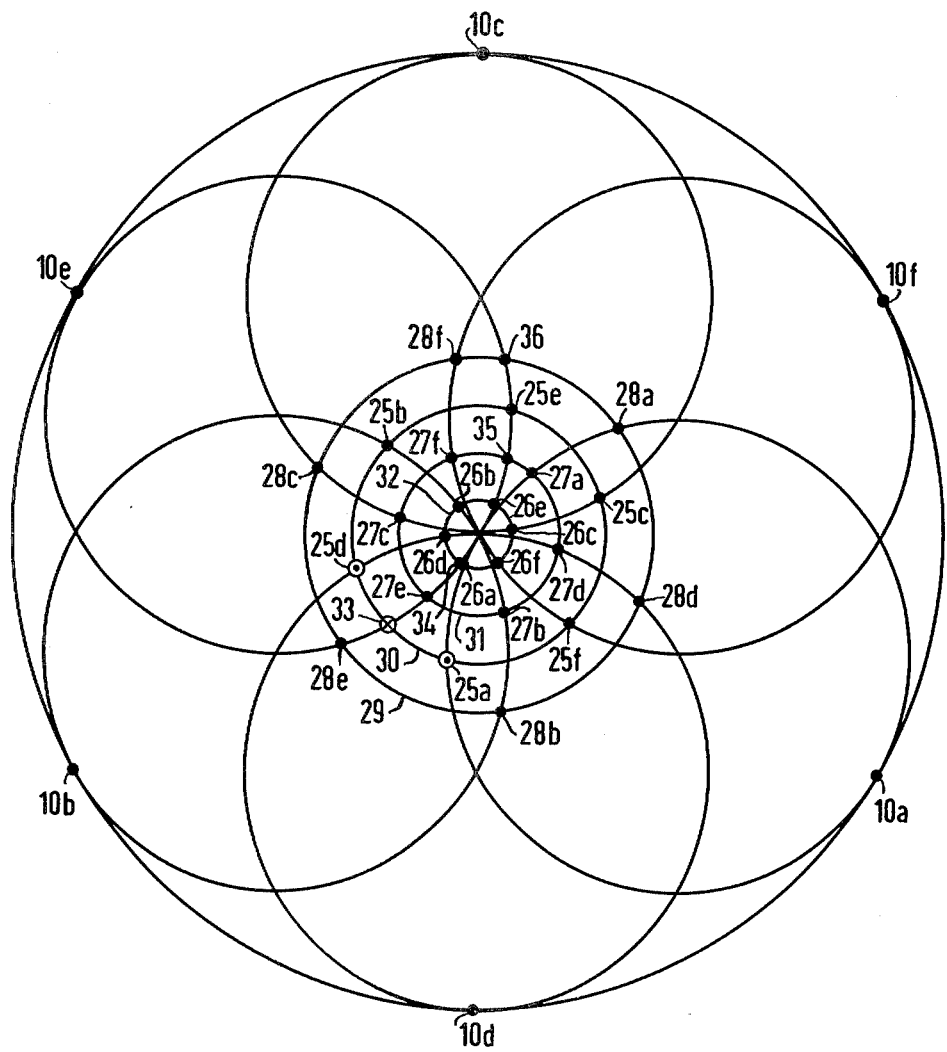

FIG. 7 now shows that by increasing the projections a calculation of intermediate data is possible. In addition to the already mentioned projections 10a to 10c with the measured value points 25a to 28c there are also three projections 10d to 10f and corresponding measured value points 25d to 28f which also lie on the measured value circles 29 to 32.

FIG. 7 shows that for the projection 10e, for example, the data of a data point 33 can be calculated; namely, from measured value data which is derived not from this projection but from other projections; and specifically by carrying out interpolation from the measured values of the measured value points 25a and 25d. Measured value data is therefore utilized from the projections 10a and 10d in order to calculate, by interpolation, the data of the data point 33 for the projection 10e. In the same way, the data of a data point lying between the data 26e and 27e can be calculated by interpolation for the projection 10e; namely, from the data of the measured value points 26a and 26d. This data point is designated by 34. Furthermore, it is possible to asscertain the data of a data point 35 for the projection 10e from the data of the measured value points 27a and 27f. Finally, it is also possible, for the projection 10e, to calculate from the data of the measured value points 28a and 28f the data of a data point 36. If the data of the projection 10e is examined, it can be seen that, through the corresponding focus, eight data points are coordinated thereto on the circle, of which four are derived from true measured values and four have been obtained by interpolation from measured values which are derived from other projections. In a similar way an intermediate value calculation by interpolation is also possible for other projections. By doubling the number of projections during a rotation of the measuring arrangement 1, 2, a doubling of the number of data points per projection is achieved when a displacement of the axes of symmetry 23a and 24a according to FIG. 5 is effected. This doubling of the number of data points corresponds to a doubling of the number of detector elements in the radiation receiver 2. Thus the possibility for a substantially more exact image calculation is created.

In order to illustrate the conception behind the invention, four detectors only are employed in the radiation receiver 2 in connection with the FIGS. 2 and 5. In practice, however, even in the case of the teaching of the invention; i.e. in the case of a mutual displacement of the axes of symmetry 23a and 24a according to FIG. 5, the number of detector elements in the radiation receiver 2 is over 100 on the order to magnitude. The detector elements may be semiconductor detectors, for example.

In FIG. 5, the measuring system may comprise a rotary frame indicated at 37 having a center of rotation or axis 38. The rotary frame mounts source 10 and the associated source collimator so that the central ray of the fan shaped beam 4 coincides with the axis of symmetry 24a of the beam. The rotary frame mounts the detector array 2 as diagrammatically illustrated in FIG. 5 so that the central ray at 24a intersects the central detector element 12 at a distance equal to one-fourth the detector separation a from the center of the detector array represented by its intersection with the axis of symmetry 23a.

It will be apparent that many modifications and variations may be effected without departing from the scope of the novel concepts and teachings of the present invention.

We claim as our invention:

1. In a tomographic apparatus for producing transverse layer image of a radiography subject including a patient couch, a radiation measuring arrangement having a radiation source which produces a fan-shaped beam of rays penetrating the radiography subject, whose cross sectional extent perpendicular to the layer plane is equal to the layer thickness and in the layer plane is of such a magnitude that the entire radiography subject is penetrated, and having a radiation receiver consisting of a row of detector elements each of which is at least partially with is said fan shaped beam and which detects the radiation intensity behind the subject, a rotary drive device for the measuring arrangement and a measured value converter for the transformation of the signals supplied by the radiation receiver into a layer image, characterized in that the radiation receiver (2) is arranged so that its axis of symmetry (23a) and the axis of symmetry (24a) of the x-ray beam (4) are always at a distance from each other in the layer plane.

2. A tomographic apparatus according to claim 1, characterized in that the distance is selected so that it corresponds to a quarter of the detector element distance.

3. A measuring system for a tomographic apparatus for producing a transverse layer image of a layer region, said apparatus including a patient couch, a radiation measuring arrangement having a radiation source for producing a substantially symmetrical fan-shaped beam of rays penetrating the layer region, and having a radiation receiver comprising a row of detector elements each of which is at least partially within said fan shaped beam and forming a substantially symmetrical array for detecting the radiation intensity from the source which is transmitted through the layer region, and means for producing successive projections by shifting the radiation source angularly about the layer region to impinge the fan-shaped beam on the layer region from successive different directions, and a measured value converter connected with the radiation receiver for the transformation of the signals supplied by the detector elements for each projection to produce a layer image, characterized in said measuring system providing an angular offset between an axis of symmetry (23a) of the radiation receiver (2) and an axis of symmetry (24a) of the fan-shaped x-ray beam (4) for each of said projections.

4. A measuring system according to claim 3 with a rotary frame mounting the x-ray source (1) and the radiation receiver (2) for joint rotation while maintaining the center of the row of detector elements offset from the point of intersection of the central ray of the fan shaped beam with the row of detector elements by a distance corresponding to one fourth of the center to center separation between detector elements.

* * * * *